(12) United States Patent
Karlsson et al.

(10) Patent No.: US 10,109,118 B2
(45) Date of Patent: Oct. 23, 2018

(54) METHOD FOR MONITORING THE OPERATION OF A SENSOR

(71) Applicant: VOLVO TRUCK CORPORATION, Gothenburg (SE)

(72) Inventors: Niclas Karlsson, Lerum (SE); Magnus Svensson, Göteborg (SE); Slavomir Nowaczyk, Halmstad (SE); Stefan Byttner, Halmstad (SE); Rune Prytz, Arlöv (SE); Thorsteinn Rögnvaldsson, Halmstad (SE)

(73) Assignee: Volvo Truck Corporation, Göteborg (SE)

( * ) Notice: Subject to any disclaimer, the term of this patent is extended or adjusted under 35 U.S.C. 154(b) by 211 days.

(21) Appl. No.: 15/026,221

(22) PCT Filed: Oct. 4, 2013

(86) PCT No.: PCT/EP2013/002983
§ 371 (c)(1),
(2) Date: Mar. 30, 2016

(87) PCT Pub. No.: WO2015/048981
PCT Pub. Date: Apr. 9, 2015

(65) Prior Publication Data
US 2016/0232723 A1 Aug. 11, 2016

(51) Int. Cl.
*G01N 33/00* (2006.01)
*G07C 5/08* (2006.01)
(Continued)

(52) U.S. Cl.
CPC ............ *G07C 5/0808* (2013.01); *F01N 11/00* (2013.01); *F02D 41/1461* (2013.01);
(Continued)

(58) Field of Classification Search
CPC ............ F02D 41/1461; F02D 41/1477; F02D 41/222; G01N 33/007; G01N 33/0037;
(Continued)

(56) References Cited

U.S. PATENT DOCUMENTS 5,088,314 A * 2/1992 Takashi ............. G01N 33/0063
236/49.3
5,423,203 A   6/1995 Namiki et al.
(Continued)

FOREIGN PATENT DOCUMENTS

CN    101341315 A    1/2009
CN    101600863 A    12/2009
(Continued)

OTHER PUBLICATIONS

Japanese Official Action (dated Jun. 19, 2017) for corresponding Japanese App. 2016-519817.
(Continued)

*Primary Examiner* — Thomas G Black
*Assistant Examiner* — Ce Li Li
(74) *Attorney, Agent, or Firm* — WRB-IP LLP (57) ABSTRACT

A method for monitoring the operation of a sensor is provided. The method comprises the step of representing the operation of the sensor by: i) storing a plurality of data values, each data value corresponding to the sensor output signal, wherein said step is performed during a time period such that said data values are distributed over a range of possible data values, ii) defining a plurality of discrete intervals within said range of possible data values; and iii) calculating the frequency of the data values within each interval thus forming a sensor representation. The method further comprises the steps of receiving at least one refer-
(Continued)

ence sensor representation; and comparing said sensor representation with said at least one reference sensor representation.

18 Claims, 5 Drawing Sheets

(51) Int. Cl.
  *F01N 11/00* (2006.01)
  *F02D 41/14* (2006.01)
  *F02D 41/22* (2006.01)
  *G05B 23/02* (2006.01)
  *F01N 3/021* (2006.01)
  *F01N 3/20* (2006.01)
(52) U.S. Cl.
  CPC ....... *F02D 41/1477* (2013.01); *F02D 41/222* (2013.01); *G01N 33/007* (2013.01); *G01N 33/0037* (2013.01); *G05B 23/0235* (2013.01); *F01N 3/021* (2013.01); *F01N 3/2066* (2013.01); *F01N 2250/02* (2013.01); *F01N 2550/00* (2013.01); *F01N 2560/026* (2013.01); *F01N 2610/02* (2013.01); *Y02A 50/245* (2018.01); *Y02T 10/40* (2013.01); *Y02T 10/47* (2013.01)
(58) Field of Classification Search
  CPC ..... G07C 5/0808; F01N 3/021; F01N 3/2066; F01N 11/00; F01N 2250/02; F01N 2250/00; F01N 2560/026; F01N 2610/02; Y02T 10/40; Y02T 10/47
  See application file for complete search history.

(56) References Cited

U.S. PATENT DOCUMENTS

| | | | | |
|---|---|---|---|---|
| 5,680,059 | A * | 10/1997 | Shiota | G01R 31/1227 324/547 |
| 5,941,918 | A * | 8/1999 | Blosser | F01N 11/00 701/31.7 |
| 7,136,705 | B1 * | 11/2006 | Park | A61N 1/36585 607/27 |
| 2010/0031633 | A1 * | 2/2010 | Kitazawa | F01N 3/0807 60/276 |
| 2010/0292959 | A1 * | 11/2010 | Gross | G06F 11/141 702/181 |
| 2011/0252767 | A1 * | 10/2011 | Lin | F01N 3/208 60/274 |
| 2014/0232539 | A1 * | 8/2014 | Hiruta | G07C 5/08 340/438 |

FOREIGN PATENT DOCUMENTS

| | | |
|---|---|---|
| CN | 102792140 A | 11/2012 |
| DE | 4108417 A1 | 9/1992 |
| DE | 19829621 A1 | 1/2000 |
| DE | 102010028852 A1 | 11/2011 |
| DE | 102012201597 A1 | 8/2013 |
| EP | 2128396 A1 | 12/2009 |
| JP | 2002196783 | 7/2002 |
| JP | 2008190383 | 8/2006 |
| JP | 2009520155 A | 5/2009 |
| JP | 2010265781 | 11/2010 |
| WO | 2007073324 A1 | 6/2007 |
| WO | 2008140381 A1 | 11/2008 |

OTHER PUBLICATIONS

International Search Report (dated Jun. 25, 2014) for corresponding International application No. PCT/EP2013/002983.
International Preliminary Report on Patentability (Jan. 25, 2016)) for corresponding International application No. PCT/EP2013/002983.
Chinese Official Action (dated May 22, 2018) for corresponding Chinese App. 15/026,221.

* cited by examiner

METHOD FOR MONITORING THE OPERATION OF A SENSOR

BACKGROUND AND SUMMARY

The present invention relates to a method and a system for monitoring the operation of a sensor. Also, the present invention relates to a method and a system for diagnosing malfunctioning systems by comparing measured values with reference values.

A modern vehicle is normally equipped with multiple systems for monitoring the actual condition of different components within the vehicle. Such vehicle components may represent relatively complex assemblies within the vehicle, such as the complete internal combustion engine or the braking system, or they may represent relatively simple elements such as individual sensors or actuators. Each component contributes to the overall performance of the vehicle and it is desirable to retrieve data corresponding to the actual operation of such components in order to detect malfunctioning and to predict maintenance.

For monitoring the actual condition of a vehicle component it is necessary to determine parameter values being associated with the actual operation of the particular vehicle component. By comparing the determined parameter values with reference values it is possible to evaluate the actual condition and to decide if the vehicle component is operating normally or not.

In WO2008/140381 a method for diagnosing malfunctioning components in a vehicle is described. In this document component-related signals describing the status of different components are used for determining a significant relation between them. The determination whether a relation is significant or not is performed by comparing the compatible relations between the different components. In case a significant relation is detected, this significant relation is compared between components, or compared for single components over time, and used as a basis on which a decision on a necessity for providing maintenance and/or repair to an individual component can be reached.

In some cases, like e.g. a single regulating component being monitored by a vehicle sensor, such particular system may be associated with a single component-related signal only, i.e. the sensor signal. Hence, it is not necessary to determine a significant relation between different component-related signals. Instead the single component-related signal may give information representing the actual condition of the vehicle component by comparing the signal parameters with reference values. Malfunction may thus be detected if the actual signal parameters are deviating from the reference values. For the vehicle system described above it may however be hard to detect a malfunction of the sensor itself. Typical sensor errors include drifting and a deteriorated step response, and should any of these errors start to occur it may no longer be possible to detect malfunctioning of the vehicle component accurately.

Therefore there is a need for an improved method for monitoring the operation of a vehicle sensor, as well as an improved method for determining the condition of a vehicle system.

It is desirable to provide an improved method and system for determining if a sensor is operating normally or not.

According to a first aspect, a method comprises the step of representing the operation of the sensor by: i) storing a plurality of data values, each data value corresponding to the sensor output signal, wherein said step is performed during a time period such that said data values are distributed over a range of possible data values, ii) defining a plurality of discrete intervals within said range of possible data values; and iii) calculating the frequency of the data values within each interval thus forming a sensor representation. Further, the method comprises the steps of:

receiving at least one reference sensor representation; and
comparing said sensor representation with said at least one reference sensor representation.

In a preferred embodiment, the system sensor is a $NO_x$ sensor of a vehicle. The method is preferably implemented for a $NO_x$ sensor due to the fact that i) the $NO_x$ sensor is a critical component for determining the status of the aftertreatment system, whereby failure may lead to increased environmental damage, and ii) the $NO_x$ sensor has a limited number of failure modes whereby the proposed method may rapidly detect malfunction in a very efficient manner.

The step of storing a plurality of data values may be performed for a plurality of different operation modes of a system to which said sensor is connected. Since the data values will most likely be different depending on different operation modes, the sensor representation will consequently have an improved statistical significance.

The reference sensor representation may include the frequency of reference data values within discrete reference intervals, said discrete reference intervals corresponding to the discrete intervals of the sensor representation.

Hence, it will be possible to compare the sensor representation with the reference representation in a simple and efficient manner.

The step of comparing said sensor representation with said reference sensor representation may further comprise the step of normalizing said representations, whereby comparison between the representations is further facilitated.

In an embodiment, the step of comparing said sensor representation with said reference sensor representation may further comprise: calculating a function representing the difference between the sensor representation and the reference sensor representation, and classifying said function according to a predetermined classification scheme. The monitoring of the sensor may thus result in a single classification, whereby the particular classification may be associated with robust information giving a clear indication of the operation of the sensor.

The classification scheme may comprise a plurality of reference categories, wherein each reference category is associated with a specific operation of the sensor. For example, this allows the reference categories to include one category corresponding to a sensor operating normally, and at least one category corresponding to a sensor operating non-normally. It may thus be possible to determine a faulty sensor in a simple manner.

The reference categories may further include one category corresponding to a sensor operating normally in a system operating normally, and at least one category corresponding to a sensor operating normally in a system operating non-normally. Hence, the method allows for system monitoring, whereby the sensor representation may not only indicate the actual status of the sensor, but also the actual status of an associated system. Should the system be a complex system for which several different fault types is possible, it may be possible to expand the bundle of reference representations to also cover different fault types for the system. Hence, a sensor representation may thus be used to identify the most similar reference representation, and to determine the actual fault type associated with the identified reference representation.

In a preferred embodiment, the system is an exhaust aftertreatment system of a vehicle. Hence, monitoring the operation of the $NO_x$ sensor may not only provide useful information regarding the actual status of the sensor itself, but also useful information regarding the operational status of the urea injection system without any direct measurements on the urea injection system.

The function representing the difference between the sensor representation and the reference sensor representation may be a scalar, whereby it is possible to provide an improved, and very robust, classification by setting specific intervals of the scalar.

In an embodiment, the method may be repeated for a plurality of times resulting in a set of functions, and further comprising the step of evaluating said set of functions for predicting malfunctioning of the sensor. It is thus possible to use the method for analyzing the behavior of the sensor and/or the associated system over time in order to predict future behavior. Hence it may be possible to determine a specific time in the future for service or maintenance thus reducing the risk for unplanned down time of the system.

The reference sensor representation may be a previous sensor representation for said sensor. The method may thus continuously store data values, whereby previously stored data values may form a reference representation.

In other embodiments, the reference sensor representation may correspond to one or several sensor representations for one or more other sensors. These other sensors may form part of different systems, e.g. different vehicles, and in a preferred embodiment the reference representation is created from data values fetched from a fleet of vehicles.

According to a second aspect, a sensor system comprises a controller for monitoring the operation of the sensor, said controller comprising a first memory configured to store a representation of the sensor operation, said sensor representation including a plurality of data values being distributed over a range of possible data values, each data value corresponding to the sensor output signal, and wherein said representation holds information relating to a frequency distribution of said data values within a plurality of discrete intervals. The controller further comprises a second memory configured to store at least one reference sensor representation, and a comparing unit configured to compare said sensor representation with said at least one reference sensor representation.

The sensor system may further comprise a communication unit configured to receive said sensor representation and said reference sensor representation from said first memory and said second memory; and to transmit said sensor representation and said reference sensor representation to said comparing unit.

The first memory may be arranged on board a vehicle, and said second memory and said comparing unit may be arranged off board a vehicle.

BRIEF DESCRIPTION OF DRAWINGS

Hereinafter, the invention will be described with reference to the appended drawings, wherein:

FIG. 3b is a histogram showing a sensor representation of a sensor operating according to the diagram shown in FIG. 3a;

FIG. 4b is a histogram showing a sensor representation of a sensor operating according to the diagram shown in FIG. 4a;

DETAILED DESCRIPTION

Figure 1:
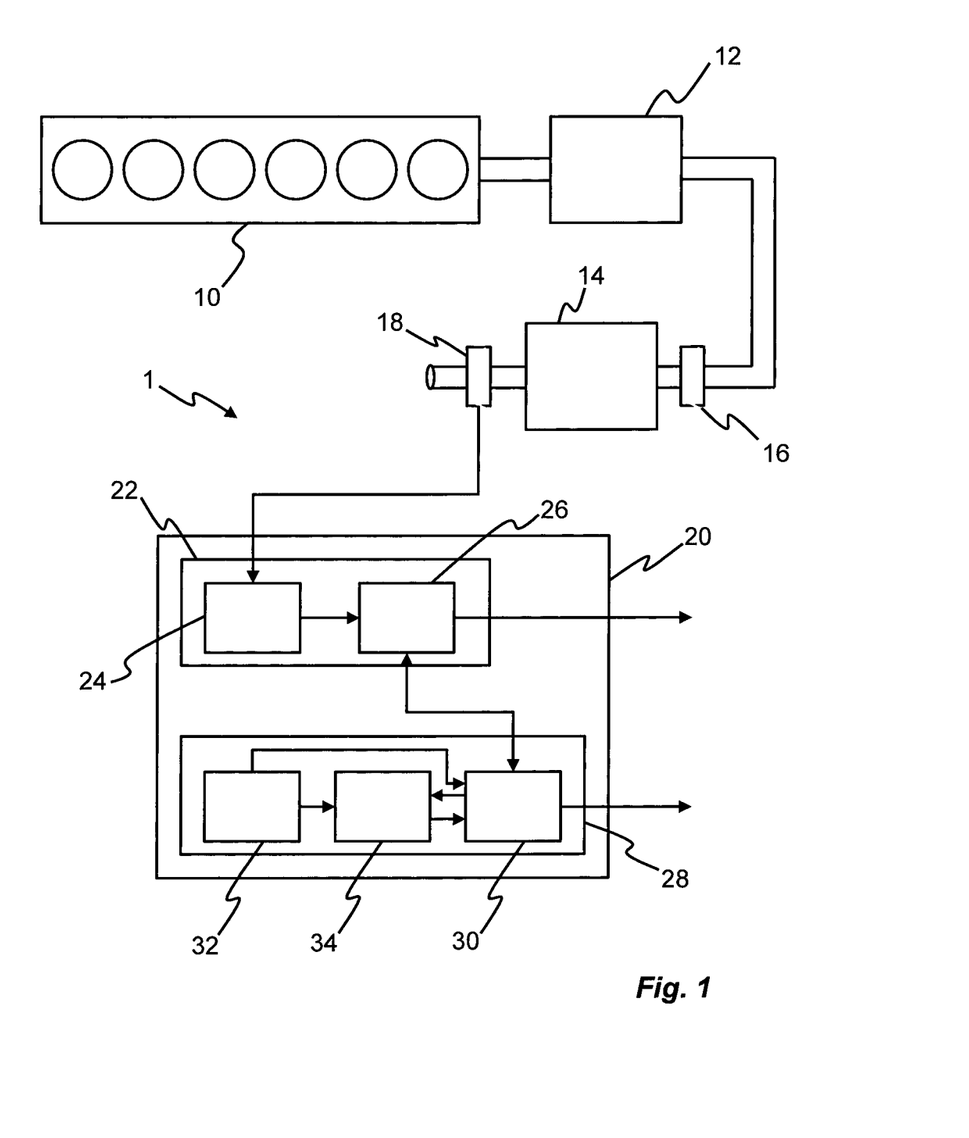
FIG. 1 is a schematic view of an aftertreatment system of a vehicle.

Starting with FIG. 1, a sensor system 1 is shown schematically. In this embodiment, the sensor system 1 forms part of a vehicle having an internal combustion engine 10. During operation, the internal combustion engine 10 emits a flow of exhaust gas which is transported through an exhaust gas aftertreatment system 12, 14 before it escapes to the environment outside the vehicle.

The aftertreatment system 12, 14 is provided in order to reduce the amount of toxic substances in the exhaust gas, and in particular the concentration of $NO_x$. For this purpose a particulate filter 12 is arranged in series with a selective catalytic reaction unit 14. The particulate filer 12 and the selective catalytic reaction unit 14 are well known in the art, especially with respect to diesel engines, and will not be described in further detail.

In order to convert hazardous $NO_x$ into diatomic nitrogen and water an urea injector 16 is used to provide a gaseous reductant in the selective catalytic reaction unit 14.

The aftertreatment system 12, 14 is monitored by a $NO_x$ sensor 18 arranged in series after the selective catalytic reaction unit 14, and before the tailpipe.

In accordance with specific embodiments, the $NO_x$ sensor is connected to a controller 20 for monitoring the operation of the $NO_x$ sensor as well as the operation of the aftertreatment system 12, 14. The controller 20 has a measurement unit 22 including a first memory 24 which is configured to store data corresponding to actual values determined by the sensor 18. The first memory 24 thus stores an amount of data corresponding to sensor output during a certain time period. Further, the measurement unit 22 includes a communication unit 26 which is configured to communicate the data of the first memory 24 with a reference unit 28.

The reference unit 28 comprises a corresponding communication unit 30 being configured to receive the data transmitted from the communication unit 26 of the measurement unit 22. Further, the reference unit 28 comprises a second memory 32 and a comparing unit 34.

The second memory 32 is configured to store data corresponding to reference values for the sensor 18. Once the communication unit 30 receives actual sensor values, or upon a command initiated externally by e.g. the ECU, the comparing unit 34 fetches these values from the communication unit 30 as well as the reference values from the second memory 32, either directly or via the communication unit 30.

The comparing unit 34 is configured to compare the actual sensor values with the reference values by forming a sensor representation of the actual data values, and a corresponding reference representation of the reference values. The sensor representation in created by defining a plurality of discrete intervals within the range of data values; and thereafter calculating the frequency of the data values within each interval. Preferably, the reference representation is created using the same discrete intervals and distributing the reference values within these intervals by calculating the frequency.

Hence, the comparing unit 34 thus compares two statistical distributions resulting in a function, or scalar, defining the difference between the sensor representation and the reference representation.

In a preferred embodiment, the sensor representation and the reference representation are histograms. In other embodiments the sensor representation and the reference representation are other probability distributions of the sensor values, such as a kernel density estimation or similar.

The comparing unit 34 is configured to output a signal representing how the sensor representation differs from the reference representation. This may be done in various ways, using e.g. the Euclidian L2-distance approach, the Hellinger distance approach, the Kullback-Leibler, or the Bhattacharyya distance approach. All these comparing algorithms are well known in the art and output a scalar representing the difference between the sensor representation and the reference representation.

In some embodiments, the comparing unit 34 is also configured to normalize the sensor representation and the reference representation before comparing.

The comparing unit 34 is further configured to transmit the output, i.e. a value or function representing the difference between the sensor representation and the reference representation, back to the communication unit 30 for further transmittal to a system monitoring unit (not shown), such as the ECU of the vehicle. This may either be done directly or via the communication device 26 of the measurement unit 22.

The controller 20 has so far been described as a two-part component, comprising a measurement unit 22 and a reference unit 28. The entire controller 20, i.e. the measurement unit 22 as well as the reference unit 28, may be arranged on board a vehicle for in-line monitoring during vehicle operation. In other embodiments, the measurement unit 22 may be arranged on board a vehicle while the reference unit 28 may be arranged off board. Hence, the communication units 26, 30 may use wireless communication, such as WiFi, to communicate. The controller 20 may be configured in various ways depending on the particular application. For example, the comparing unit 34 may be arranged within the measurement unit 22 instead of the reference unit 28.

In order to provide significant accuracy during comparison it is advantageous to include a specific amount of data in the sensor representation. Hence, the sensor representation includes sensor data for a number of different modes of the aftertreatment system. Since the NOx concentration varies with different driving modes it is advantageous to add sensor data during long term, such that measuring sensor data is performed during a time period long enough for the data values to be distributed over the complete range of possible data values. In a vehicle application measuring sensor data may typically involve one or several weeks of data collection such that many different driving characteristics, and consequently many different $NO_x$ concentrations, will occur.

The method described above may not only be utilized in order to determine the actual condition of the aftertreatment system 12, 14, but also for determining the actual condition of the sensor 18.

Figure 2A:
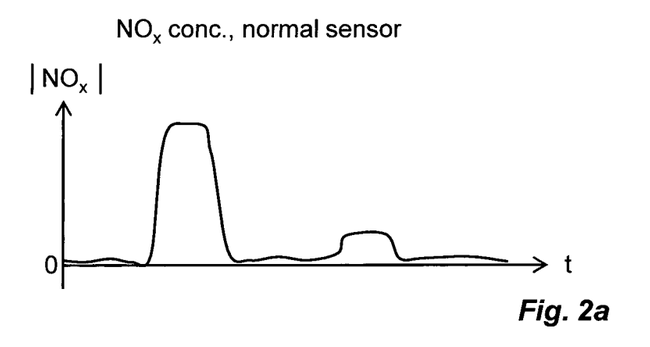
FIG. 2a is a diagram showing the NOx concentration for a sensor operating normally.

With reference to FIG. 2a, the actual $NO_x$ concentration in the exhaust gas after selective catalytic reaction is shown during a specific time period. As can be seen in the diagram, the concentration is close to zero, but increases during two occasions. Such occasions may represent specific driving behavior. Starting at the left end of the diagram, the initial period, in which the concentration lies close to zero, may represent normal driving. The first peak may represent a cold start, whereby the second peak may represent a higher load on the internal combustion engine.

When the $NO_x$ sensor is operating normally the measured sensor values are equal to, or very close to, the actual concentration.

Figure 2B:
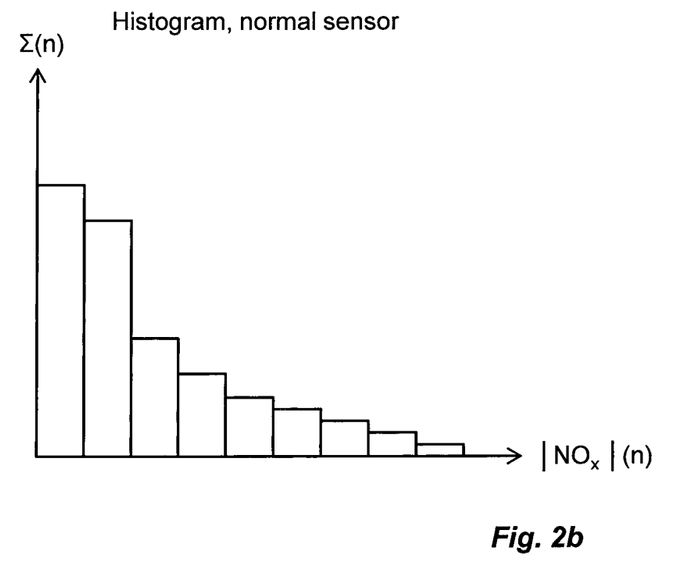
FIG. 2b is a histogram showing a sensor representation according to an embodiment.

When sampling is made during long term as has been described above, a typical sensor representation is shown in FIG. 2b. The major amount of data values are in the bin closest to zero, and the frequency of higher concentrations decrease rapidly due to the fact that such concentrations occur rarely. Should the sampling period be extended there would be no significant change in the statistical distribution, since the relationship between the different frequencies would be the same. On the other hand, should the sampling period be shortened, there is a risk that some concentrations only occurring during extreme conditions would be left out, thus changing the histogram slightly.

The $NO_x$ sensor is a critical component which may be subject to damage or malfunction, resulting in erroneous concentration values. This is far from ideal, since the sensor may in those cases no longer provide accurate information regarding the actual emission of $NO_x$.

It has been discovered that a NOx sensor may malfunction in two different ways; either by drifting or by a slower response.

Figure 3A:
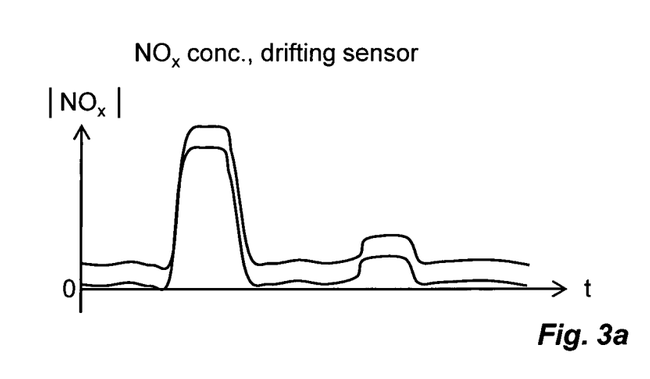
FIG. 3a is a diagram showing the NOx concentration for a sensor operating non-normally.
Figure 3B:
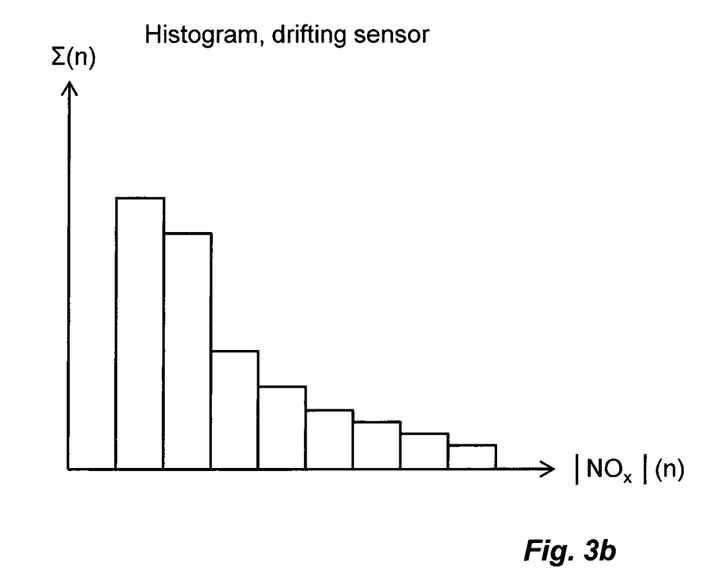

A drifting sensor is schematically shown in FIG. 3a. Here, the actual concentration is shown as the solid line being equal to the solid line shown in FIG. 2a. However, as the sensor has been damaged its zero level has changed, resulting in data values representing higher concentrations. A long term sampling would thus result in a sensor representation shown in FIG. 3b. Since the zero level has changed, the entire histogram has been shifted to the right.

Figure 4A:
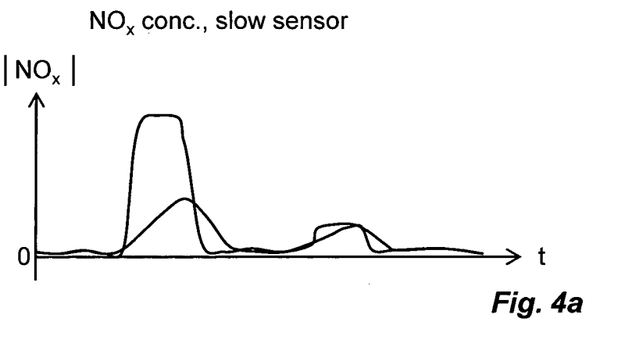
FIG. 4a is a further diagram showing the NOx concentration for a sensor operating non-normally.
Figure 4B:
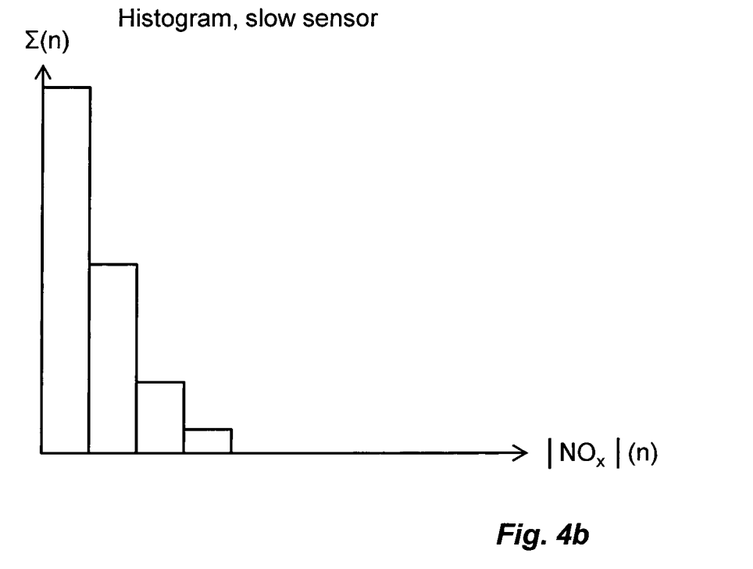

A slow sensor is schematically shown in FIG. 4a. Here, the actual concentration is shown as the solid line being equal to the solid line shown in FIGS. 2a and 3a. However, as the sensor has been damaged its response is slower, resulting in data values representing concentrations which no longer correspond to actual concentrations during rapid changes. A long term sampling would thus result in a sensor representation shown in FIG. 4b. Since the sensor is slow, the histogram has been truncated and no longer includes any values in the bins corresponding to higher $NO_x$ concentrations.

Hence, by comparing the sensor representation with a reference representation, like the one shown in FIG. 2b corresponding to a sensor operating normally, it will be possible to actually determine if the sensor is operating normally or not. In a further embodiment it may also be possible to actually determine in what way the sensor is operating non-normally. For this purpose the reference representation may in fact be two different reference representations, one for each fault mode i.e. one reference representation for a slow sensor and one reference representation for a drifting sensor. By comparing the sensor representation with the drifting sensor reference representation as well as with the slow sensor reference representation it may be possible to determine the best match, thus indicating the type of fault of the sensor.

Figure 5:
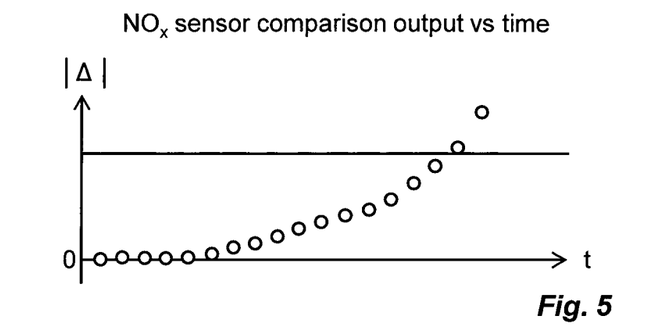
FIG. 5 is a diagram showing functions as a result of comparing a sensor representation with a reference representation according to an embodiment.

Now turning to FIG. 5, a diagram describing the comparison output over time will be described. The Y-axis represents the difference between the sensor representation and the reference representation, and the X-axis represents time. By performing the method during operation it will be possible to predict maintenance of the sensor. This is due to the fact the sensor rarely becomes damaged at a specific time, but instead degrades continuously. As can be seen in FIG. 5, the result of the comparison starts close to the zero level, implying that the comparing unit has implemented a comparison algorithm for which a perfect match corresponds to zero. After some time, which may correspond to several hundreds of hours driving, the sensor starts to degrade whereby the result of the comparison starts to increase. The increase is not linear over time, but accelerates whereby the sensor eventually is far from its original calibration. By having set a predetermined threshold corresponding to a comparison result for which the sensor is considered to be malfunctioning, it is possible to predict the need for maintenance. This threshold is indicated by the dashed line in FIG. 5.

Figure 6:
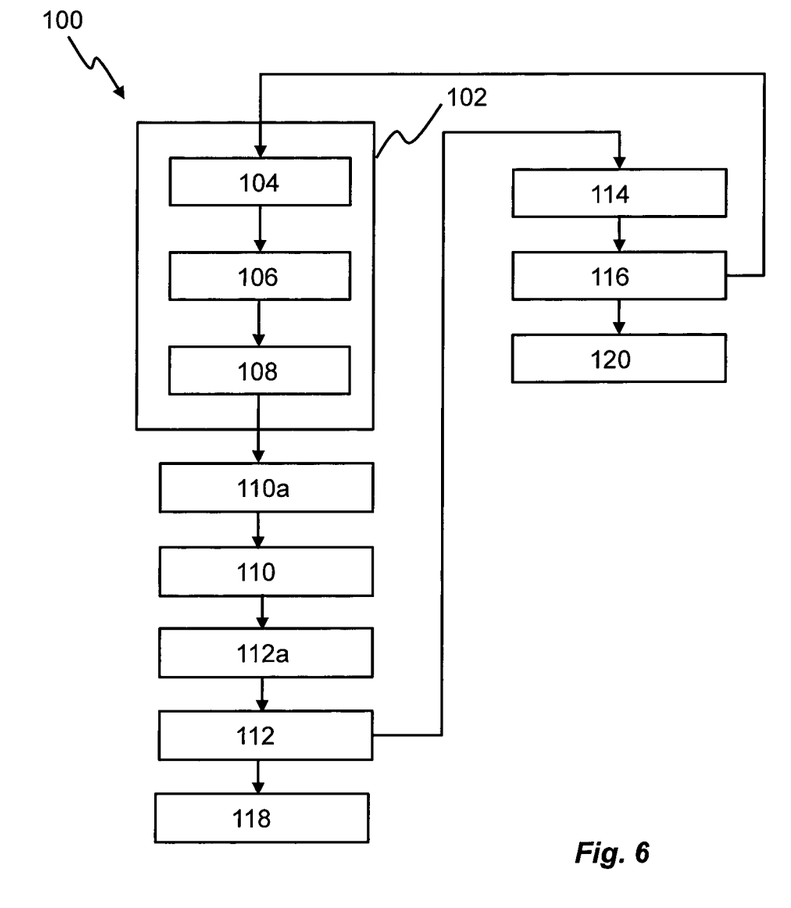
FIG. 6 is a schematic view of a method according to an embodiment.

Now turning to FIG. 6, a method 100 according to an embodiment will be discussed. The method comprises a first step 102 of representing the operation of the sensor, which preferably is a $NO_x$, sensor in an aftertreatment system of a vehicle. This is made by a sequence of individual steps, starting with a step 104 of storing a plurality of data values, each data value corresponding to the sensor output signal. Step 104 is performed during a specific period of time, such that the data values are distributed over a range of possible data values. In a subsequent step 106 the method 100 defines a plurality of discrete intervals within the range of possible data values whereby the method 100 continues by calculating the frequency of the data values within each interval in step 108. At this point, a sensor representation is formed as a statistical distribution.

The method continues by a step 110 in which at least one reference sensor representation is received, which step 110 is followed by a step 112 of comparing the sensor representation with the at least one reference sensor representation.

In specific embodiments step 110 further comprises the sub-step 110a of creating the reference representation by arranging the frequency of reference data values within discrete reference intervals, wherein the discrete reference intervals correspond to the discrete intervals of the sensor representation. It should be noted that step 110a and step 106, 108 could be performed in reversed order, such that the sensor representation is created with the same intervals as the already created reference representation.

Step 112 may be preceded by a step 112a in which the sensor representation and the reference representation are normalized prior to comparing them.

Further, step 112 of comparing the representations may include a number of sub-steps. A step 114 may be performed in which a function, such as a scalar, representing the difference between the sensor representation and the reference sensor representation is calculated, and a further step 116 may be performed in which the function is classified according to a predetermined classification scheme.

As a result from step 116, the classification scheme may comprise a plurality of reference categories, wherein each reference category is associated with a specific operation of the sensor. For example, the reference categories include one category corresponding to a sensor operating normally, and at least one category corresponding to a sensor operating non-normally. The reference categories may also include one category corresponding to the sensor operating normally in a system operating normally, and at least one category corresponding to the sensor operating normally in a system operating non-normally.

This provides for additional advantages whereby the monitoring of the sensor operation may actually provide information of the current operation of the associated system. For example, the second memory 32 described with reference to FIG. 1 may include a plurality of reference representations, wherein each reference representation is valid for a specific sensor operation (i.e. normal operation, non-normal operation due to drifting, or non-normal operation due to slow response, etc) and a specific system operation (i.e. normal operation of the urea injector 16, non-normal operation of the urea injector 16, etc.). All reference representations may have a significant statistical distribution, whereby the comparing unit 34 may be configured to compare the sensor representation with each one of the available reference representations. It will thus be possible to identify the reference representation which provides the best match with the sensor representation, thus indicating the most probable operation of the sensor as well as of the associated system.

The described method 100 may be repeated for a plurality of times resulting in a set of functions, such as scalars, and it may further comprise the step 118 of evaluating said set of functions for predicting malfunctioning of the sensor. In case of system monitoring by monitoring the operation of the sensor, the method may also comprise a step 120 of evaluating said set of functions for predicting malfunctioning of the system.

Although the description has been mainly directed to a method and system for monitoring the operation of a $NO_x$ sensor in an aftertreatment system of a vehicle, it should be understood that the method and system may also be utilized for monitoring the operation of various kinds of sensors, as well as systems being associated with such sensors.

It will be appreciated that the embodiments described in the foregoing may be combined without departing from the scope as defined by the appended claims.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", etc do not preclude a plurality.

The invention claimed is:

1. A method of monitoring NOx, comprising:
monitoring NOx in an exhaust aftertreatment system of a vehicle with a NOx sensor;
identifying malfunctions in the NOx sensor by monitoring operation of the NOx sensor, comprising the steps of:
representing the operation of the sensor by:
i) storing a plurality of data values, each data value corresponding to a sensor output signal, wherein the step is performed during a time period such that the data values are distributed over a range of possible data values,
ii) defining a plurality of discrete intervals within a range of possible data values; and
iii) calculating a frequency of the data values within each interval thus forming a sensor representation;
receiving at least one reference sensor representation; and
comparing the sensor representation with the at least one reference sensor representation.

2. The method according to claim 1, wherein the step of storing a plurality of data values is performed for a plurality of different operation modes of a system to which the sensor is connected.

3. The method according to claim 1, wherein the reference sensor representation includes a frequency of reference data values within discrete reference intervals, the discrete reference intervals corresponding to the discrete intervals of the sensor representation.

4. The method according to claim 3, wherein the step of comparing the sensor representation with the reference sensor representation further comprises the step of normalizing the representations.

5. The method according; to claim 1, wherein the step of comparing the sensor representation with the reference sensor representation further comprises:
    calculating a function representing the difference between the sensor representation and the reference sensor representation, and
    classifying the function according to a predetermined classification scheme.

6. The method according to claim 5, wherein the classification scheme comprises a plurality of reference categories, wherein each reference category is associated with a specific operation of the sensor.

7. The method according to claim 1, wherein the reference categories include one category corresponding to a sensor operating normally, and at least one category corresponding to a sensor operating non-normally.

8. The method according to claim 7, wherein the reference categories further include one category corresponding to a sensor operating normally in a system operating normally, and at least one category corresponding to a sensor operating normally in a system operating non-normally.

9. The method according to claim 8, wherein the system is an exhaust aftertreatment system of a vehicle.

10. The method according to claim 1, wherein the function is a scalar.

11. The method according to claim 1, wherein the method is repeated for a plurality of times resulting in a set of functions, and further comprising the step of evaluating the set of functions for predicting malfunctioning of the sensor.

12. The method according to claim 1, wherein the reference sensor representation is a previous sensor representation for the sensor.

13. The method according to claim 1, wherein the reference sensor representation corresponds to one or several sensor representations for one or more other sensors.

14. A computer comprising program code for performing the steps of claim 1 when the program is run on the computer.

15. A non-transitory computer readable medium carrying a computer program for performing the steps of claim 1 when the program is run on a computer.

16. A sensor system, comprising
    a NOx sensor of a vehicle, and
    a controller for identifying malfunctions in the NOx sensor by monitoring operation of the sensor, the controller comprising
        a first memory storing a representation of the sensor operation, the sensor representation including a plurality of data values being distributed over a range of possible data values, each data value corresponding to a sensor output signal, and wherein the representation holds information relating to a frequency distribution of the data values within a plurality of discrete intervals,
        a second memory storing at least one reference sensor representation, and
        a comparing unit configured to compare the sensor representation with the at least one reference sensor representation.

17. The sensor system according to claim 16, further comprising a communication unit configured to receive the sensor representation and the reference sensor representation from the first memory and the second memory and to transmit the sensor representation and the reference sensor representation to the comparing unit.

18. The sensor system according to claim 17, wherein the first memory is arranged on board a vehicle, and wherein the second memory and the comparing unit are arranged off board a vehicle.

* * * * *